United States Patent
Vierra et al.

[11] Patent Number: 5,807,243
[45] Date of Patent: Sep. 15, 1998

[54] METHOD FOR ISOLATING A SURGICAL SITE

[75] Inventors: Mark A. Vierra, Woodside; Alex T. Roth, Redwood City, both of Calif.

[73] Assignee: Heartport, Inc., Redwood City, Calif.

[21] Appl. No.: 603,175

[22] Filed: Feb. 20, 1996

Related U.S. Application Data

[62] Division of Ser. No. 298,646, Aug. 31, 1994, abandoned.

[51] Int. Cl.⁶ .................................................. A61B 1/313
[52] U.S. Cl. ....................... 600/204; 600/205; 600/235; 128/898
[58] Field of Search .................................. 600/201, 204, 600/205, 208, 210, 235; 606/191, 158, 157; 128/898

[56] References Cited

U.S. PATENT DOCUMENTS

| | | |
|---|---|---|
| 3,503,398 | 3/1970 | Fogarty et al. . |
| 3,515,129 | 6/1970 | Truhan . |
| 4,245,638 | 1/1981 | Lebeck et al. .......................... 128/346 |
| 4,492,229 | 1/1985 | Grunwald . |
| 4,635,636 | 1/1987 | Goldstein .............................. 128/334 |
| 4,834,090 | 5/1989 | Moore . |
| 4,854,318 | 8/1989 | Solem et al. ........................... 128/346 |
| 4,946,463 | 8/1990 | Wright . |
| 5,037,428 | 8/1991 | Picha et al. ............................ 606/155 |
| 5,167,223 | 12/1992 | Koros et al. ....................... 600/211 X |
| 5,195,506 | 3/1993 | Hulfish . |
| 5,197,948 | 3/1993 | Ghodsian . |
| 5,300,087 | 4/1994 | Knoepfler . |
| 5,318,579 | 6/1994 | Chow . |
| 5,374,277 | 12/1994 | Hassler . |
| 5,447,515 | 9/1995 | Robicsek ............................... 606/158 |
| 5,452,733 | 9/1995 | Sterman et al. . |

FOREIGN PATENT DOCUMENTS

| | | | |
|---|---|---|---|
| 782804 | 11/1980 | U.S.S.R. | ............................... 606/157 |
| WO 95/01757 | 1/1995 | WIPO . | |

OTHER PUBLICATIONS

Pilling Co., Pilling Surgical Instruments Catalog, 1993, p. 304: "Riahi Coronary Compressor".

Primary Examiner—Jeffrey A. Smith
Attorney, Agent, or Firm—Jeffry J. Grainger; Jens E. Hoskendijk; Michael J. Lynch

[57] ABSTRACT

The invention provides a system and method for performing less-invasive surgical procedures within a body cavity. In a preferred embodiment, the invention provides a system and method for isolating a surgical site such as an anastomosis between an internal mammary artery and a coronary artery in a thoracoscopic coronary artery bypass grafting procedure. The system comprises a foot (11) pivotally coupled to the distal end of a shaft (3) by a linkage (13). The foot has first and second engaging portions (15, 17) with contact surfaces for engaging a tissue surface. The engaging portions are movable between an open position, where the contact surfaces are separated by a gap, and a collapsed position, where the foot is configured for delivery through the percutaneous penetration. An actuator, at the proximal end of the shaft, can be rotated to pivot the foot about a transverse axis so that the contact surfaces are oriented generally parallel to the surgical site to apply pressure to the tissue structure on both sides of the surgical site.

40 Claims, 7 Drawing Sheets

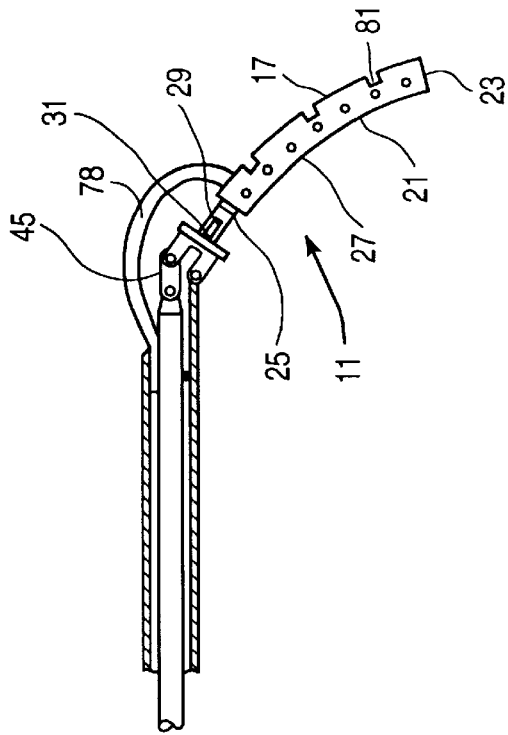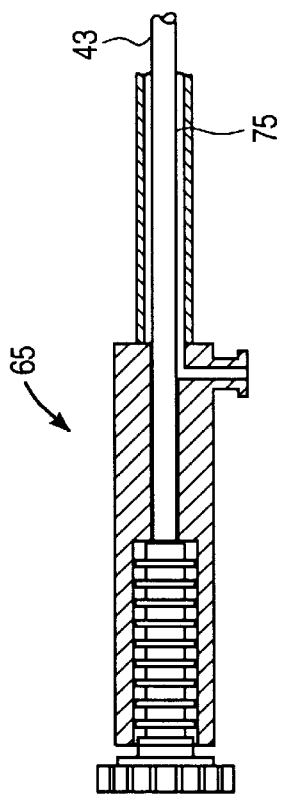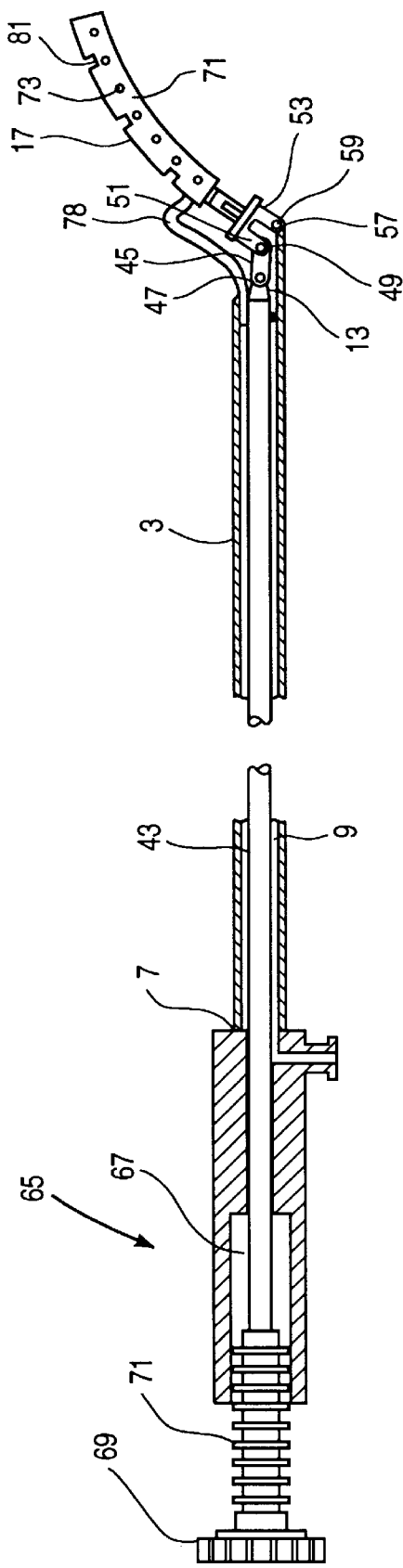
FIG. 2A
FIG. 2B

1

METHOD FOR ISOLATING A SURGICAL SITE

This is a Division of application Ser. No. 08/298,646 filed Aug. 31, 1994, which is now abandoned in favor of file wrapper continuing application Ser. No. 08/686,073 (pending).

FIELD OF THE INVENTION

This invention relates generally to a system and method for performing less-invasive surgical procedures, and more specifically, to a system and method for isolating a surgical site such as the site of an anastomosis of a graft vessel and a coronary artery in a thoracoscopic coronary artery bypass grafting procedure.

BACKGROUND OF THE INVENTION

In coronary artery disease, the build-up of artherosclerotic plaque on the inner walls of the coronary arteries causes a narrowing or complete closure of these arteries, resulting in insufficient blood flow to the heart. This condition has become one of the most common life-threatening medical problems facing older men and women.

A number of approaches have been developed for treating coronary artery disease. In less severe cases, it is often sufficient to treat the symptoms with pharmaceuticals and lifestyle modification to lessen the underlying causes of the disease. In more severe cases, a coronary artery blockage can often be treated using endovascular techniques such as balloon angioplasty, atherectomy, laser or hot tip ablation, placement of stents, and the like.

In cases where pharmaceutical treatment and/or endovascular approaches have failed or are likely to fail, it is often necessary to perform a coronary artery bypass graft procedure using open surgical methods. Such methods require that the patient's sternum be divided longitudinally and the chest be spread apart to provide access to the heart, known as a median sternotomy. The patient's heart is placed under cardioplegic arrest and the patient is supported by cardiopulmonary bypass. A source of arterial blood is then connected to the diseased coronary artery downstream from the blockage. The arterial blood source may be a venous or arterial graft vessel connected between an arterial blood vessel such as the aorta and the coronary artery. Another common arterial blood source is either the left or right internal mammary artery which may be grafted to the coronary artery which is narrowed or occluded. Recent studies have suggested that the use of the mammary arteries as an arterial blood source may be advantageous over other sources due to a greater likelihood that the graft will remain patent over time.

To form an anastomosis between an internal mammary artery and a coronary artery, blood flow through the internal mammary artery must be temporarily stopped, typically by applying a removable clamp to the mammary artery. The mammary artery is then severed downstream from the clamp to create a free end. An incision is created in the target coronary artery downstream of the blockage. The free end of the mammary artery can then be connected to the incision in the coronary artery, typically by suturing, such that blood can flow from the mammary artery through the incision into the coronary artery.

To facilitate the surgeon's view of the procedure, the heart must be positioned to expose the anastomosis site, and the anastomosis site must be cleared of fluids, tissue and debris which may obscure the site. In addition, the coronary artery or mammary artery may contain blood and other fluids near the location of the incision, which should be prevented from flowing out of the coronary artery or mammary artery during the suturing procedure. The coronary and mammary arteries must also be stabilized and held in a stationary position so that the surgeon can perform the delicate task of sewing the free end of the mammary artery to the coronary artery.

Using conventional open-chest methods, the anastomosis procedure is typically performed directly through the large opening in the patient's chest provided by a median sternotomy. This opening enables the surgeon to see the coronary and mammary arteries directly and to position his or her hands within the chest cavity in close proximity to these arteries for manipulation of surgical instruments. The surgeon can thus utilize various instruments to reposition the heart, clear away fluid and debris and stabilize the anastomosis site during the procedure. For example, clamps may be applied to the mammary and coronary vessels to stop blood from leaking from these vessels. If tissue or fluids migrate into the anastomosis site, the surgeon can utilize an irrigation tube to wash these obstructions away from the site. The heart may be repositioned using retraction devices or simply by hand. To stabilize the mammary artery during the anastomosis, a pair of forceps can be used to grasp the mammary artery and maintain its position while it is sewn to the coronary artery. All of these tasks are accomplished without great difficulty due to the open exposure of the surgical site through the large opening provided by a median sternotomy.

While open-chest coronary artery bypass grafting is very effective in many cases, the gross thoracotomies used in conventional open heart surgery to perform coronary artery bypass grafting are highly traumatic to the patient. Therefore, new methods of performing surgery on the heart using minimally invasive thoracoscopic techniques have been recently developed. In these methods, the patient's heart is arrested by occluding the patient's aorta between the coronary arteries and the brachiocephalic artery with an expandable balloon on the distal end of an endovascular catheter introduced via a femoral artery. Cardioplegic fluid is then delivered to the patient's myocardium through a lumen in the same catheter or through a separate catheter positioned in the coronary sinus. This method allows the surgeon to perform operations such as coronary artery bypass grafting without creating a large opening in the patient's sternum. Minimally-invasive cutting and suturing instruments can be introduced thoracoscopically to connect the free end of the severed mammary artery to the coronary artery. Complete descriptions of such methods are found in commonly assigned U.S. Pat. 5,452,733 and application Ser. No. 08/194,946, filed Feb. 11, 1994, now U.S. Pat. No. 5,501,698, which are incorporated herein by reference.

The new generation of thoracoscopic methods of performing coronary artery bypass grafting has, of course, created many new challenges. Such challenges include keeping the anastomosis site free of fluid and debris, positioning the heart within view of the surgeon(s), and stabilizing the coronary and mammary arteries to facilitate the anastomosis. These functions must be performed through small percutaneous incisions or cannulae positioned in intercostal spaces in the patient's rib cage. Known devices are not capable of performing these tasks through small percutaneous penetrations and, therefore, are unsuitable for closed chest procedures.

For this reason, improved systems and methods are desired for isolating a surgical site, such as an opening in a fluid-carrying vessel, in a body cavity via a small percutaneous incision or cannula. Preferably, the system and method would be capable of isolating a site of an anastomosis between a coronary artery and a mammary artery during a coronary artery bypass grafting procedure. The system and method should allow the surgeon to apply pressure against a vessel on both sides of an opening or incision in the vessel to inhibit blood and other fluids from passing through the incision. The system and method should also allow the surgeon to stabilize the mammary artery to facilitate suturing the free end of the mammary artery to the coronary artery. The system and method should further allow the delivery of irrigation fluids to the surgical site to wash away fluid and debris. In addition, it would be desirable if the above functions were performed by a single instrument introduced through a cannula or small percutaneous incision to limit the number of incisions required to perform the procedure.

SUMMARY OF THE INVENTION

The present invention provides an endoscopic device and method for isolating a surgical site, such as an opening in a fluid-carrying vessel, through a small, percutaneous penetration in the patient. The invention allows the surgeon to position a contact surface against a vessel and exert pressure against the vessel to inhibit blood and other fluids from flowing through an opening in the vessel. The contact surface is also adapted to stabilize a second vessel for attachment to the first vessel. In addition, the invention may be used to hold an end of a suture while performing a surgical procedure such as an anastomosis. The invention further allows the delivery of an irrigation fluid to the surgical site to clear away blood and debris. The system is particularly suited for forming an anastomosis between a coronary artery and an internal mammary artery in a thoracoscopic coronary artery bypass procedure. While being especially suited for thoracoscopic procedures, the system and method of the invention are also useful in other surgical procedures, such as laparoscopic, endoscopic and arthroscopic procedures, as well as in conventional open surgical procedures.

In one aspect of the invention, the system comprises a shaft having a proximal end and a distal end configured for delivery through a small, percutaneous penetration. A foot, configured for engaging a tissue structure such as a blood vessel, is pivotally coupled to the distal end of the shaft. The foot has first and second engaging portions separated by a gap. The engaging portions each have a contact surface for engaging the tissue structure such that a surgical site on the tissue structure is disposed in the gap. A linkage is coupled to the foot, and an actuator means, coupled to the proximal end of the shaft, actuates the linkage to pivot the foot about a transverse axis so that the contact surfaces may be oriented generally parallel to the surface of the tissue structure. This allows the surgeon to apply pressure to the tissue structure on two sides of the surgical site The tissue structure may be, for example, a blood vessel to which a second blood vessel is to be attached in an anastomosis procedure. An opening will be formed in the blood vessel to which the second blood vessel is to be connected. The first and second engaging portions of the foot may be positioned so that the opening in the blood vessel is disposed in the gap. In this way, the contact surfaces on the engaging portions may be pressed against the blood vessel to close the vessel lumen, thereby stopping the flow of blood and other fluids through the opening. At the same time, the foot stabilizes the blood vessel to maintain its position during the procedure. Additionally, the second blood vessel may be positioned under one or both contact surfaces to hold it in position as it is attached to the other vessel. Further, the foot may be used to reposition the blood vessel to improve access and/or visibility of the surgical site.

In a preferred embodiment, the linkage includes a longitudinal rod slidably disposed within an axial lumen in the shaft and having proximal and distal ends. The proximal end of the rod is coupled to the actuator means and the distal end of the rod is coupled to the foot. The foot is coupled to the shaft at a pivot point and to the rod at a coupling point separated from the pivot point. Axial movement of the rod with respect to the shaft rotates the foot about the pivot point. Preferably, the foot can pivot more than 90 degrees about the transverse axis so that the surgeon can approach the surgical site from various directions.

The actuator means is configured to pivot the foot about the transverse axis from a first position, where the foot is configured for delivery through a percutaneous penetration, to a second position, where the contact surfaces are oriented generally parallel to the surgical site. In an exemplary embodiment, the actuator means comprises a knob threadably coupled to the proximal end of the shaft. The knob is fixed to the proximal end of the rod so that rotation of the knob moves the knob and the rod in an axial direction with respect to the shaft.

In one embodiment, the foot comprises first and second arms extending distally from the distal end of the shaft. The arms are movable between an open configuration, where the arms are disposed apart, and a collapsed configuration, where the arms are disposed closer together. In the open configuration, the arms form a "V" shape and are configured to engage the blood vessel on both sides of the opening. In the collapsed configuration, the arms are substantially parallel so that the foot is configured for delivery through a percutaneous penetration in the patient's body. The arms may be biased into the open configuration by a spring, or an actuator may be used for moving the arms between the open and collapsed configurations.

In a second embodiment, the foot comprises an annular ring with an inner hole. The hole preferably has a diameter larger than the opening in the vessel so that the annular ring can engage the vessel on both sides of the opening without obstructing the opening. Preferably, the annular ring is made of a flexible material so that it can be collapsed into a configuration suitable for introduction through a percutaneous penetration. Alternatively, the annular ring includes a hinge so that the ring can be folded into a collapsed configuration.

The invention may further include means for retaining a suture in contact with the foot. Preferably, the suture retaining means is a plurality of slots formed in upper surfaces of the foot for frictionally engaging the suture. The suture will include first and second free ends each connected to a needle. The first free end may be placed in and retained by one of the slots while the surgeon manipulates the second free end. The second free end may then be placed in and retained by one of the slots while the surgeon utilizes the first free end. If desired, the surgeon can apply tension to the suture by rotating the foot. This allows the surgeon to reposition or stabilize the surgical site during the operation.

For the purpose of removing fluids and debris from the surgical site, the shaft includes an irrigation lumen extending between the distal and proximal ends and the foot includes a plurality of holes fluidly coupled to the lumen at the distal end. The proximal end of the lumen is configured for being coupled to a source of irrigation fluid to allow the fluid to be delivered under positive pressure through the lumen and through the holes in the foot to the surgical site. The holes are preferably configured and positioned to direct irrigation fluid into the gap between the first and second engaging portions to clear fluid and debris from the surgical site. If desired, a reservoir of fluid can be created within the hole in the annular ring to submerge the surgical site in fluid during the surgical procedure.

The invention is also useful for repositioning an organ in a body cavity to facilitate a surgical procedure. For example, the invention is useful for repositioning the heart in a coronary artery bypass grafting procedure. To reposition the heart, the foot is introduced through a percutaneous incision or trocar sleeve and pivoted relative to the shaft so that the contact surfaces are generally parallel to the external surface of the heart. Preferably, the contact surfaces on the arms of the foot have an arcuate portion that generally conforms to the curvature of the heart. The surgeon then applies a force to the foot to frictionally engage the heart and reposition it to the desired location for the surgical procedure. To reduce the risk of damaging the heart and to augment the frictional contact force, an atraumatic high friction material, such as foam, may be attached to the contact surfaces.

The invention is particularly useful for isolating an anastomosis site between a coronary artery and an internal mammary artery during a cardiac procedure such as coronary artery bypass grafting. In this procedure, the patient's heart is placed under cardioplegic arrest and the patient is supported by cardiopulmonary bypass. Several cannulae are positioned in percutaneous intercostal penetrations in the left anterior chest of the patient. A viewing scope is introduced through another left anterior percutaneous intercostal penetration. A small incision is made in the left lateral chest, through which instruments are introduced to dissect a portion of a mammary artery away from the chest wall. The mammary artery is clamped and then severed to create a free end downstream of the clamp. An incision is created in the coronary artery corresponding to the size of the free end of the mammary artery.

Once the mammary and coronary arteries are prepared for the anastomosis, the engaging portions of the foot are moved into the collapsed configuration and introduced through the cannula. After the foot has passed through the cannula, the engaging portions are biased back into the open configuration. The knob is then rotated to actuate the linkage and pivot the foot such that the contact surfaces are generally parallel to the surface of the heart and the wall of the target coronary artery. The shaft is advanced distally until the contact surfaces engage the coronary artery so that the incision in the artery lies in a gap between the arms. Although normal blood flow through the coronary artery will have stopped since the heart will have been placed under cardioplegic arrest, the cardioplegic fluid used to stop the heart may continue to flow through the coronary arteries during the procedure. The foot is pressed against the artery with sufficient force to inhibit fluids from flowing through the incision in the coronary artery. Preferably, a free end of the mammary artery is also placed under the contact surface of the foot to stabilize the mammary artery and hold the free end in a stationary position with respect to the incision in the coronary artery.

A suture is then introduced to sew the free end of the mammary artery to the coronary artery. To facilitate the operation, the first free end of the suture can be retained in one of the slots on the foot while suturing the vessels with the second free end. During the operation, fluid may be periodically delivered through the irrigation lumen and the holes in the foot to wash away fluids and other debris that may have migrated into the anastomosis site. If desired, a reservoir of fluid may be maintained on the wall of the heart between the contact portions of the foot to keep the opening in the coronary artery submerged during the procedure, thereby preventing the introduction of air into the coronary arteries. After the anastomosis has been completed, the foot is withdrawn from the surgical site and removed from the patient's body through the cannula.

It should be understood that while the invention is described in the context of thoracoscopic surgery of the heart, the system and method disclosed herein are equally useful in other types of surgery, e.g. surgery on vessels and organs within the abdomen or pelvis.

A further understanding of the nature and advantages of the invention may be realized by reference to the remaining portions of the specification and the drawings.

BRIEF DESCRIPTION OF THE DRAWINGS

FIGS. 2A and 2B are side cross-sectional views of a shaft coupled to a foot of the endoscopic device of FIG. 1, illustrating the foot pivoted into different positions with respect to the shaft;

DETAILED DESCRIPTION OF SPECIFIC EMBODIMENTS

Figure 1:
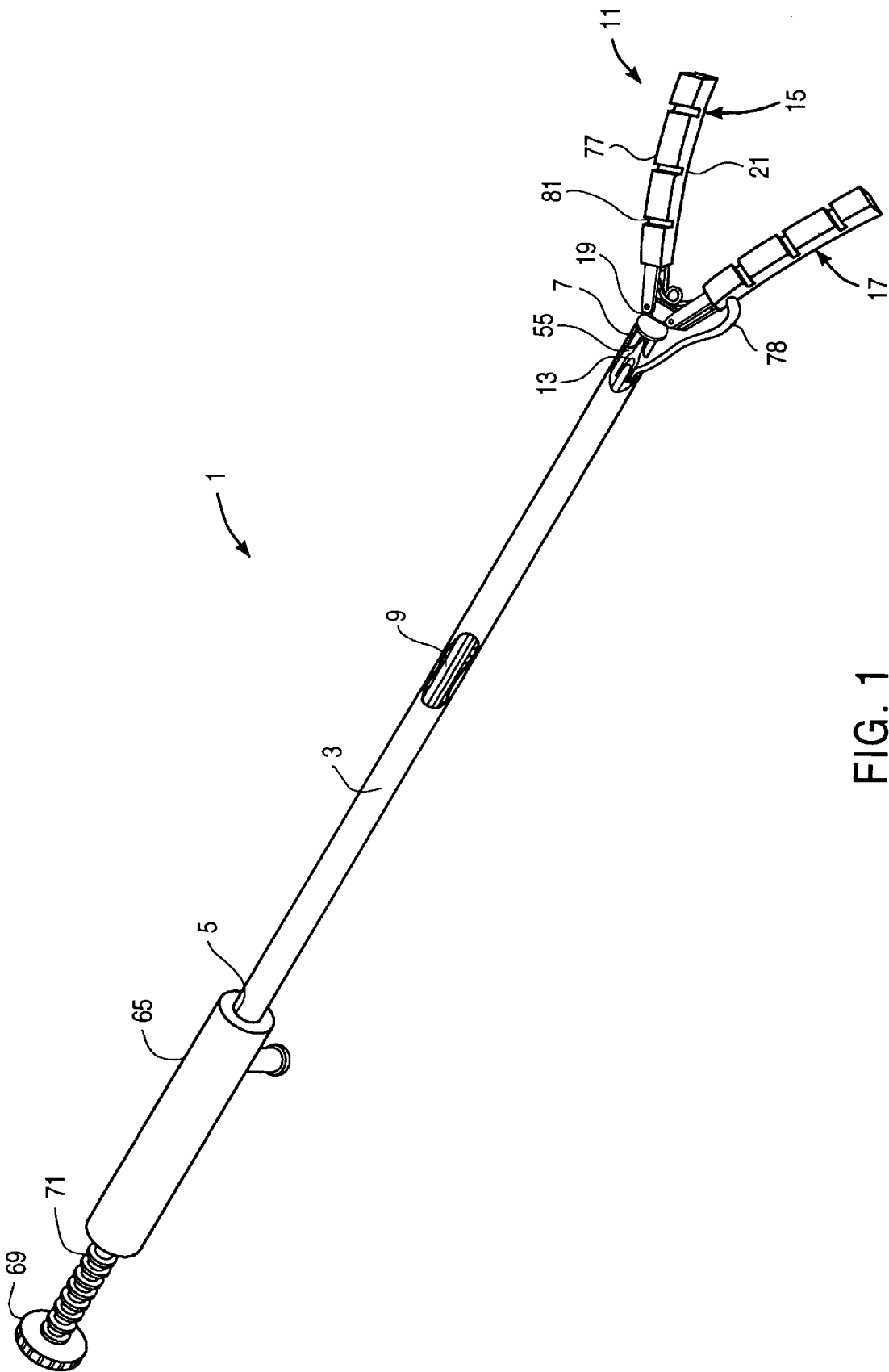
FIG. 1 is a perspective view of an endoscopic device according to the present invention.

The system and method of the present invention for isolating a surgical site will now be described in detail. Referring to FIG. 1, an endoscopic device 1 includes a shaft 3 having a proximal end 5, a distal end 7 and an axial passage 9 therebetween. Shaft 3 is preferably a stainless steel tube having an outer diameter in the range of 2–10 mm, usually 4–8 mm, so as to fit within a cannula having an internal diameter in the range of 2–15 mm. Shaft 3 can also be introduced directly through a percutaneous incision in the patient. Shaft 3 has a length selected to reach a target site in a body cavity, such as the abdomen or thoracic cavity, and to extend sufficiently out of the body cavity to facilitate easy manipulation of endoscopic device 1. Thus, shaft 3 should be at least between 10 cm and 40 cm and is preferably between 17 cm and 30 cm. It should be noted that although shaft 3 is shown as having a circular cross-sectional shape in the drawings, shaft 3 could alternatively have a rectangular, triangular, oval or channel cross-sectional shape.

A foot 11 is pivotally coupled to distal end 7 of shaft 3 by a linkage 13 (discussed in greater detail below). Foot 11 comprises first and second arms 15, 17 pivotally mounted to a coupling member 19. As shown in FIGS. 2A and 2B, first and second arms 15, 17 each include an engaging portion 21 having a distal end 23 and a proximal end 25. Engaging portions 21 each have an inner contact surface 27 for engaging a tissue structure such as a fluid-carrying vessel or an organ such as the heart. Contact surfaces 27 preferably have a curvature selected to approximately conform to the curvature of the outer surface of the heart in the region of the coronary artery targeted in a bypass grafting procedure (described in further detail below). Thus, contact surfaces 27 will usually extend along an arc of a circle having a radius between 2–10 cm, preferably between 3–5 cm. Contact surfaces 27 can be alternatively shaped to conform with other organs or tissue structures with which the invention is to be used.

Figure 3A:
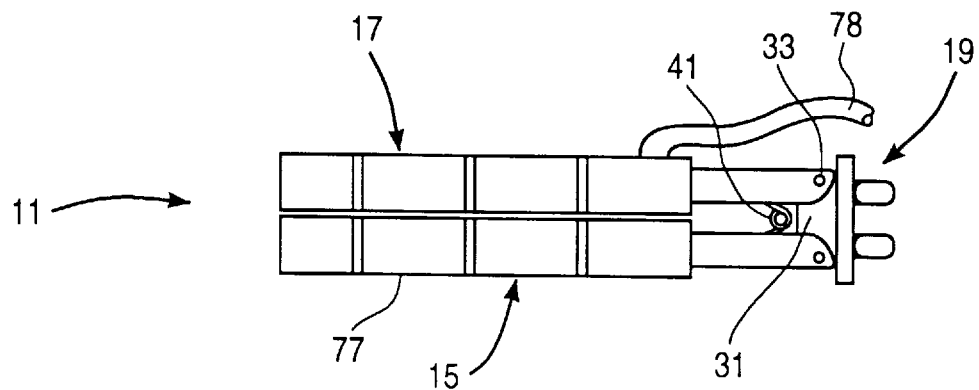
FIGS. 3A and 3B are top views of the foot of FIGS. 2A and 2B, illustrating first and second arms of the foot in the open and closed positions.
Figure 3B:
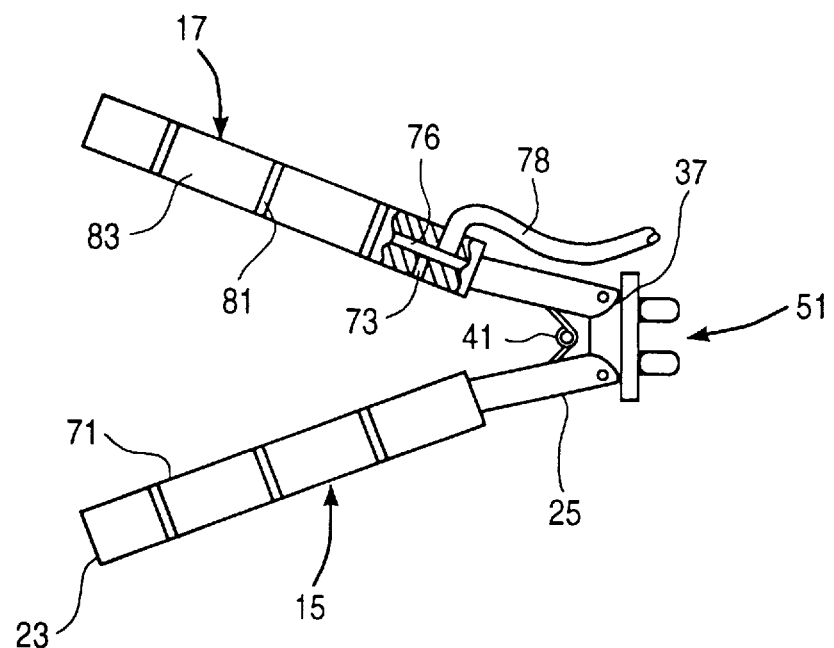

Proximal ends 25 of arms 15, 17 each have a slot 29 which receives a tongue 31 of coupling member 19. As shown in FIGS. 3A and 3B, proximal ends 25 are each rotatably coupled to tongue 31 by a pin 33. This configuration allows arms 15, 17 to pivot between an open position, where the arms 15, 17 are disposed apart in a general V-shape (FIG. 3B) to a collapsed position, where the arms 15, 17 are closer together and generally parallel (FIG. 3A). It should be noted that the invention is not limited to the above configuration and a variety of conventional coupling mechanisms can be used to rotatably couple arms 15, 17 to coupling member 19.

Proximal ends 25 each have a proximal surface 37 shaped so as to limit the movement of arms 15, 17 beyond the open position shown in FIG. 3B. A torsion spring 41 biases arms 15, 17 into the open position. In the open position, arms 15, 17 will preferably be oriented at an angle between 15 and 50 degrees from each other and usually between 35 and 45 degrees. In an exemplary embodiment, arms 15, 17 have a length of 40 to 60 mm. In this manner, arms 15, 17 may engage both sides of an opening in a blood vessel, for example, or two different vessels that are separated by a distance of 10–50 mm.

Arms 15, 17 will be substantially parallel in the collapsed position so that foot 11 has a maximum cross-sectional width of 5–20 mm and preferably less than 12 mm. In this way, foot 11 can be delivered through a small percutaneous penetration when arms 15, 17 are in the collapsed position. To introduce foot 11 through such a penetration, arms 15, 17 may be urged together and held in the collapsed position as the surgeon guides foot 11 through the incision. If the percutaneous penetration is a trocar sleeve or cannula, the inner walls of the cannula will maintain arms 15, 17 in the collapsed position as foot 11 passes through the cannula. Once foot 11 has passed completely through the cannula or incision, spring 41 will force arms 15, 17 into the open position. Alternatively, an actuator mechanism located at proximal end 7 of shaft 3 may be provided to allow the surgeon to selectively open and close arms 15, 17. In this manner, arms 15, 17 could be held in the collapsed position until foot 11 is within the body cavity.

Referring again to FIG. 1, FIGS. 2A and 2B, linkage 13 comprises a longitudinal rod 43 slidably disposed within shaft 3 and a link 45 having first and second ends 47, 49. Coupling member 19 has a bifurcated proximal end with first and second coupling points 51, 53. First end 47 of link 45 is coupled to the distal end of rod 43 and second end 49 of link 45 is coupled to coupling member 19 at coupling point 51. Shaft 3 has an angled opening 55 at distal end 5 to allow arms 15, 17 to pivot into an orientation transverse to shaft 3. Second coupling point 53 of coupling member 19 is pinned to distal end 57 of shaft 3 to form a pivot point 59. Foot 11 pivots about a transverse axis through pivot point 59.

In the above described configuration, axial movement of rod 43 with respect to shaft 3 will pivot foot 11 about pivot point 59. As illustrated in FIGS. 2A and 2B, foot 11 can be pivoted at least 90 degrees and preferably over 120 degrees with respect to shaft 3. For example, the surgeon may pivot foot 11 upwards with respect to shaft 3 and push shaft 3 in the distal direction to press engaging portions 21 of foot 11 against the tissue surface. If the tissue surface has a different orientation (i.e. facing away from the surgeon), the surgeon may pivot foot 11 downwards with respect to shaft 3 and pull shaft 3 in the proximal direction to press engaging portions 21 against the tissue surface.

A handle 65 having a threaded inner bore 67 is coupled to proximal end 7 of shaft 3. A knob 69 is fixed to a threaded rod 71 that mates with threaded inner bore 67 so that rotation of knob 69 moves knob 69 and threaded rod 71 in an axial direction with respect to shaft 3. The distal end of threaded rod 71 is connected to the proximal end of rod 43. Thus, clockwise rotation of knob 69 slides rod 43 and link 45 in the distal direction thereby pivoting coupling member 19 and foot 11 about an axis transverse to the longitudinal axis of shaft 3. Counterclockwise rotation of knob 69 slides rod 43 and link 45 in the proximal direction thereby causing coupling member 19 and foot 11 to pivot in a reverse direction. Note that handle 65 may alternatively include another type of actuator mechanism such as a plunger mechanism, a pair of scissor-type handles, or a slidable button within a longitudinal slot in handle 65.

In a preferred embodiment, arms 15, 17 have inner surfaces 71 with a plurality of irrigation holes 73, as shown in FIG. 2B. Holes 73 are in communication with an inner lumen 76 in arm 17. Shaft 3 includes an irrigation lumen 75, which may comprise lumen 9, a separate lumen in shaft 3, or a lumen within rod 43, that is fluidly coupled to lumen 76 by a flexible tube 78, as shown in FIG. 3B. The proximal end of irrigation lumen 75 is configured for coupling to a source of irrigation fluid so that the fluid can be delivered under positive pressure through lumen 75, lumen 76 and then through holes 73 to the surgical site. Any conventional fluid source that delivers fluid at a low pressure can be connected to lumen 75 such as an intravenous drip bag. Alternatively, irrigation lumen 75 can be coupled to a vacuum source to suction fluids from the surgical site out of the patient.

To avoid the possibility of damaging the tissue surface when arms 15, 17 are pressed against it, foot 11 includes atraumatic means on contact surfaces 27 of arms 15, 17. Preferably, the atraumatic means comprises an elastomeric sleeve 77 around engaging portion 21 of arms 15, 17, as shown in FIGS. 3A. Sleeve 77 can be constructed of any soft, elastomeric material such as rubber, soft plastic, foam or surgical gauze, but is preferably made of silicone. The durometer of sleeves 77 is preferably within the range of 30 to 80 Shore A. Suitable sleeves are commercially available from Sil-Med Corp of Taunton, Mass. under the trade name "Vascular Paws".

Referring again to FIGS. 3A and 3B, sleeves 77 have a number of slots 81 formed in a top surface 83. Slots 81 are adapted to frictionally engage a portion of a suture during a surgical procedure. Thus, slots 81 preferably have a width of about 0.5–2.0 mm. This allows the surgeon to place one end of the suture in a slot during the procedure to hold the suture end while the surgeon manipulates the other end of the suture. Preferably, sleeves 77 each have 3–4 slots so that the surgeon may place the suture at a convenient location along either arm 15, 17.

Figure 4A:
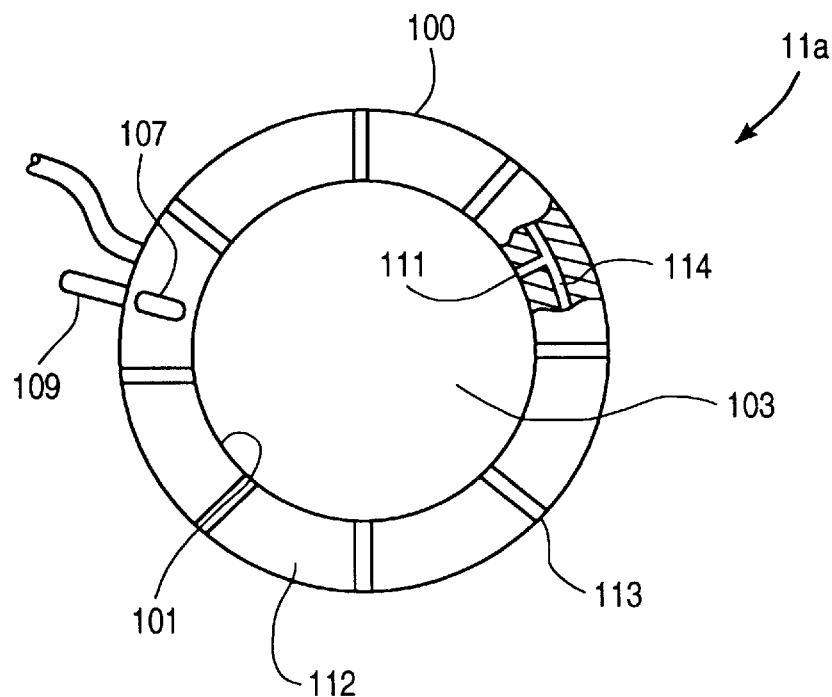
FIGS. 4A and 4B are side and top views, respectively, of an alternative embodiment of a foot according to the invention.
Figure 4B:
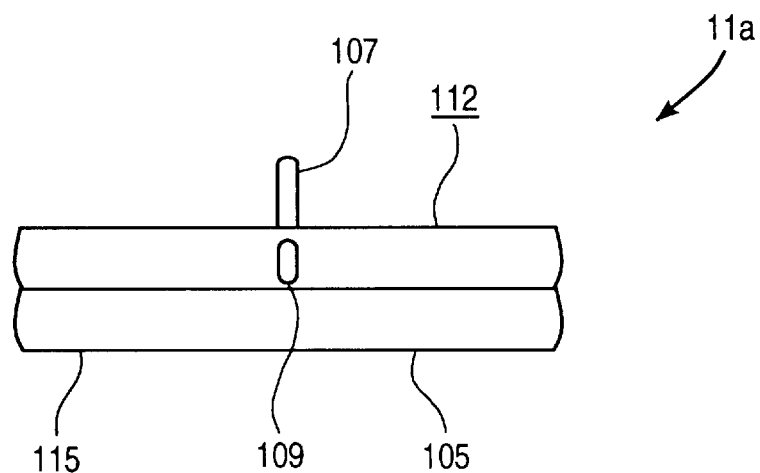

FIGS. 4A and 4B illustrate an alternative embodiment of foot 11 according to the invention. In this embodiment, foot 11*a* comprises an annular ring 100 having an inner circumferential surface 101 surrounding a hole 103. Foot 11a further includes a bottom contact surface 105 for engaging the tissue structure so that the surgical site lies within hole 103. Foot 11a has first and second coupling points 107, 109 for pivotally coupling foot 11a to shaft 3 similarly to foot 11 described above in the preferred embodiment. Foot 11a is well-suited for engaging a fluid-carrying vessel having an opening through which fluid could flow out of the vessel. Hole 103 has a diameter larger than the opening in the vessel so that annular ring 100 engages the vessel on both sides of the opening without obstructing the opening. Preferably, hole 103 will have a diameter from 5 to 50 mm, usually between 20 mm and 40 mm. Ring 100 will preferably have a thickness between 2 mm and 10 mm.

Preferably, foot 11a is made of a flexible material such as rubber so that annular ring 100 can be collapsed into a configuration suited for introduction through a small percutaneous incision or cannula. In this configuration, the surgeon collapses annular ring 100 so that foot 11a has a smaller cross-sectional profile and then introduces foot 11a through the incision or cannula. Annular ring 11a then expands into its original circular shape once it has passed through the percutaneous penetration. Alternatively, foot 11a may include a hinge (not shown) so that a portion of annular ring 100 could be folded around the hinge to decrease the cross-sectional profile of annular ring 100. In this configuration, foot 11a could be made of a more rigid material such as stainless steel or tungsten carbide.

Foot 11a has a plurality of holes 111 on inner circumferential surface 101. Holes 111 are fluidly coupled to an inner lumen 114 in communication with irrigation lumen 75 in shaft 3 for delivery of irrigation fluid to the surgical site. If desired, sufficient fluid may be introduced to create a fluid reservoir within hole 103 to submerge the surgical site. This enables the surgeon to conduct the surgical procedure within the fluid reservoir to inhibit air from entering the surgical site. For example, if the surgical site is an incision in a fluid-carrying vessel, the fluid reservoir could help prevent air from entering the vessel through the incision.

A plurality of slots 113 are provided on an upper surface 112 of ring 100. Slots 113 are configured to frictionally engage a suture, as discussed above. Slots 113 are spaced around annular ring 100, thereby allowing the surgeon to apply tension to the suture in various directions.

Foot 11a further includes atraumatic means attached to ring 100 to prevent damage to the vessel. Preferably, the atraumatic means in this embodiment is a soft fabric pad 115 such as that obtainable from Scanlan of St. Paul, Minn. under the brand name "Fabric Clamp Covers". Other atraumatic means may also be used, such as a foam pad with a thickness of 5–10 mm.

It should be understood that foot 11 could have a variety of shapes and configurations so long as it comprises two relatively rigid portions with bottom surfaces suitable for engaging a tissue structure and separated by a gap so as to engage the tissue structure at two laterally separated locations on both sides of a surgical site.

The invention may be used in a variety of surgical procedures within body cavities. The invention is particularly well adapted for facilitating the anastomosis of two fluid carrying vessels, such as the anastomosis of a coronary artery and a graft vessel in a coronary artery bypass grafting procedure.

A method for forming an anastomosis between a coronary artery and an internal mammary artery in a coronary artery bypass grafting procedure according to the invention will now be described in conjunction with FIGS. 5–7. A more complete description of a thoracoscopic coronary artery bypass grafting procedure can be found in commonly assigned U.S. Pat. No. 5,452,733 and application Ser. No. 08/194,946, filed Feb. 11, 1994, now U.S. Pat. No. 5,501,698, which have been incorporated herein by reference. The patient undergoing the procedure is placed under general anesthesia and prepared in a conventional manner for cardiac surgery. In a preferred embodiment, a plurality of access trocar sleeves will be positioned in percutaneous intercostal penetrations for introduction of foot 11 and other surgical instruments. It should be noted that the terms "percutaneous intercostal penetration" and "intercostal penetration" as used herein refer to any penetration, in the form of a small cut, incision, hole or cannula, trocar sleeve or the like, through the chest wall between two adjacent ribs which does not require cutting, removing, or significantly displacing or retracting the ribs or sternum. Usually, the percutaneous penetration will require a puncture or incision of less than about 5 cm in length.

In a preferred embodiment, the trocar sleeves will be positioned within intercostal spaces in the left lateral chest of the patient, generally within the second, third, fourth, fifth, sixth or seventh intercostal spaces. To facilitate the isolation of the surgical site, foot 11 will preferably be introduced through a percutaneous intercostal penetration in either the third or fourth intercostal space. The trocar sleeves will generally be introduced between adjacent ribs and will penetrate with their proximal end disposed just above the superior rib surfaces.

Although trocar sleeves are described as the preferred method of introducing instruments into the thoracic cavity, other similar methods may be employed. For example, foot 11 can be introduced directly through a small percutaneous intercostal incision in the patient's chest. Trocar sleeves are preferred, however, to provide an open passage into the thoracic cavity and to protect adjacent tissue from injury.

Figure 5:
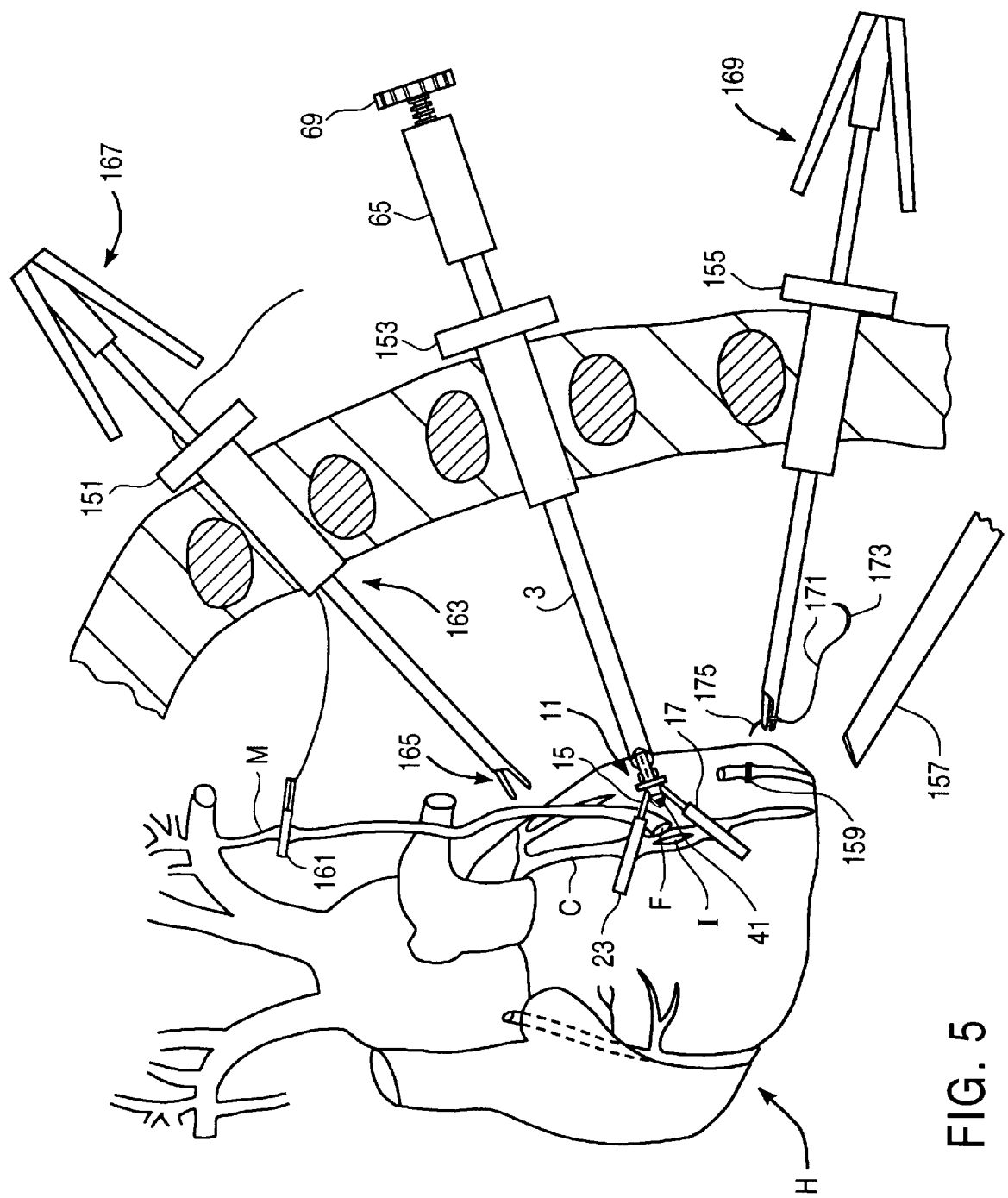
FIG. 5 is a schematic illustration showing the endoscopic device of FIG. 1 isolating a surgical site of an anastomosis of a coronary artery and a left internal mammary artery in a thoracoscopic coronary artery bypass grafting procedure.

Three trocar sleeves 151, 153, 155 are illustrated in FIG. 5. The trocar sleeves 151, 153, 155 used for cardiac surgery will generally be shorter than those used for conventional laparoscopic procedures. Typically, trocar sleeves useful for the present invention will have a length in the range from about 2–10 cm, and an internal diameter in the range from 2–15 mm. Suitable trocar sleeves are available from United States Surgical Corp. of Norwalk, Conn., under the brand name "Thoracoport"™. In addition, the trocar sleeves can be flexible to permit better manipulation of tools introduced therethrough.

The invention will be described in reference to the left anterior descending coronary artery C and the left internal mammary artery M, as shown in FIG. 5. The left internal mammary artery is suitable as an arterial source for target locations on the left anterior descending coronary artery, the diagonal coronary artery, the circumflex artery/obtuse marginal artery, and the ramus intermedius coronary artery. The invention is also suitable for use on the right internal mammary artery. The right internal mammary artery is available for connection to all of the same target locations, as well as the right coronary artery and the posterior descending artery.

As shown in FIG. 5, a viewing scope 157 is introduced through a trocar sleeve (not shown) to a position suitable for viewing the target location on coronary artery C. Viewing scope 157 can be any conventional viewing scope such as an endoscope, laparoscope, or thoracoscope, which typically consist of a rigid, elongated tube containing a lens system and an eyepiece or camera mount at the proximal end of the tube. A small video camera is preferably attached to the camera mount and connected to a video monitor to provide a video image of the procedure. Alternatively, the invention can be practiced with a viewing scope having a guidable tip that can be rotated by manipulation from a proximal end of the tube. This type of scope is commercially available from Baxter Healthcare Corp. of Deerfield, Ill.

As an alternative to the above viewing systems, a visualization system for direct, stereoscopic visualization of the thoracic cavity could be utilized, as described in commonly assigned, co-pending application Ser. No. 08/135,387, filed Oct. 8, 1993, now abandoned or in co-pending application Ser. No. 08/227,365, filed Apr. 13, 1994, now U.S. Pat. No. 5,588,949 which are incorporated herein by reference. This visualization system comprises a surgical microscope coupled to an access cannula. The access cannula can be positioned percutaneously in an intercostal space, facilitating direct stereoscopic visualization through the access cannula into the chest cavity. This system provides high image quality and the natural hand-eye coordination of direct vision while allowing multiple persons to simultaneously view the surgical site.

Before the anastomosis procedure begins, the left lung will be collapsed to facilitate viewing of the operation. Known techniques for collapsing the lung can be used such as introducing a tube through the trachea into the right main stem bronchus and applying a vacuum through the tube. After the lung is collapsed, a length of mammary artery M is dissected from the inner thoracic wall with a conventional electrosurgical tool (not shown) introduced through one of the trocar sleeves 151, 153, 155. A clip 159 is then applied downstream of the region of the mammary artery M that will be transected. Clip 159, which may be a conventional surgical clip, serves to permanently cut off the lower portion of mammary artery M downstream of clip 159 from the blood stream. Suitable clips can be obtained from Weck surgical instruments of Largo, Fla. under the brand name HEMOCLIP.

To prepare mammary artery M for the anastomosis, a releasable clamp 161 is introduced through trocar sleeve 151 by an introducing instrument (not shown). The jaws of clamp 161 are closed onto mammary artery M to temporarily stop the flow of blood downstream of clamp 161. Preferably, the introducing instrument releases clamp 161 and is removed from the patient's body. This method for occluding the mammary artery is described in greater detail in commonly assigned, co-pending application Ser. No. 08/265,477 filed Jun. 24, 1994, titled Endoscopic Vascular Clamping System and Method, now U.S. Pat. No. 5,569,274 which is incorporated herein by reference. After mammary artery M has been clamped, it is severed at a location downstream of clamp 161 with a conventional cutting instrument (not shown). Note that it will be desirable to cut mammary artery M along a diagonal transverse line in order to provide an oval-shaped free end F to facilitate connection to coronary artery C.

After mammary artery M has been prepared and clamped, the heart will be arrested and the patient placed on cardiopulmonary bypass. It should be understood, however, that these steps could be performed before mammary artery M is transected. Arterial and venous cannulae are introduced into a femoral artery and a femoral vein, respectively, and connected to a cardiopulmonary bypass pump and oxygenation system. The patient's aorta is then partitioned at a location between the brachiocephalic artery and the coronary ostia. Preferably, this partitioning is achieved by endovascularly advancing the distal end of a catheter to the desired location within the ascending aorta and expanding a balloon on the catheter to inhibit the flow of blood and other fluids past this location. The patient's heart will then be stopped, typically by introducing cardioplegic fluid into the isolated heart through the aortic occlusion catheter with the patient's circulation maintained by cardiopulmonary bypass. This method for arresting the heart and establishing cardiopulmonary bypass is described in greater detail in commonly assigned, co-pending applications, Ser. Nos. 07/991,188, filed Dec. 15, 1992, now abandoned and 08/123,411, filed Sep. 17, 1993, now abandoned which are incorporated herein by reference.

Once the patient's heart has been arrested, an incision I is made in the wall of coronary artery C downstream from an occluded or narrowed region therein. Incision I is made with dimensions selected to match those of the free end F of mammary artery M. Typically, mammary artery will have a radius between 3-5 mm. It should be noted, however, that the coronary artery may be connected to a variety of venous or arterial graft vessels from other portions of the patient's body. In these cases, incision I will generally conform to the dimensions of the selected arterial blood source.

Although normal blood flow through coronary artery C will have stopped since the heart has been placed under cardioplegic arrest, the cardioplegic fluid used to stop the heart will continue to flow through the coronary arteries during the procedure. This cardioplegic fluid may force blood and other fluids through incision I or the cardioplegic fluid itself may flow directly through incision I.

At this point in the procedure, foot 11 may be introduced through trocar sleeve 153, as shown in FIG. 5. Arms 15, 17 are moved together into the collapsed position and distal ends 23 of arms 15, 17 are placed into trocar sleeve 151. The inner wall of trocar sleeve 151 maintains arms 15, 17 in the collapsed position as foot 11 is guided into the body cavity. After arms 15, 17 have passed through trocar sleeve 151, spring 41 will automatically force arms 15, 17 back into the open position.

When foot 11 is suitably positioned over incision I, the surgeon rotates knob 69 to pivot foot 11 relative to shaft 3 until contact surfaces 23 of engaging portions 21 of arms 15, 17 are generally parallel to the surface of heart H in the region of coronary artery C. The surgeon then applies pressure to foot 11 to engage coronary artery C with contact surfaces 23 of arms 15, 17 so that incision I lies within the gap between arms 15, 17. Preferably, the surgeon will apply enough force to inhibit blood and other fluids from flowing through incision I. Once coronary artery C has been suitably engaged by contact surfaces 23 of foot 11, handle 65 or shaft 3 may be clamped to a clamping fixture mounted to the operating table (not shown) to fix the position of shaft 3 relative to the body cavity. Alternatively, shaft 3 can be introduced through a locking cannula that will clamp onto shaft 3 thereby securing its position with respect to the tissue structure.

It may be necessary to retract or rotate the patient's heart H to enhance the surgeon's view of the procedure or to facilitate the anastomosis procedure. The surgeon may apply a force to foot 11 to frictionally engage the heart. As discussed above, arcuate portions 21 of arms 15, 17 generally conform to the curvature of the heart to facilitate the repositioning of the heart and to prevent contact surfaces 23 from damaging the heart. The heart can be repositioned into a suitable location for the anastomosis procedure by manipulating handle 65.

After the surgical site has been isolated, a grasping instrument 163 and a needle holding instrument 167 are introduced through trocar sleeves 151 and 155, respectively. Gripping instrument 163 moves free end F of mammary artery M into position for the anastomosis. Needle holding instrument 169 holds a sufficient length of suture 171 having first and second needles 173, 175 on either end.

Figure 6:
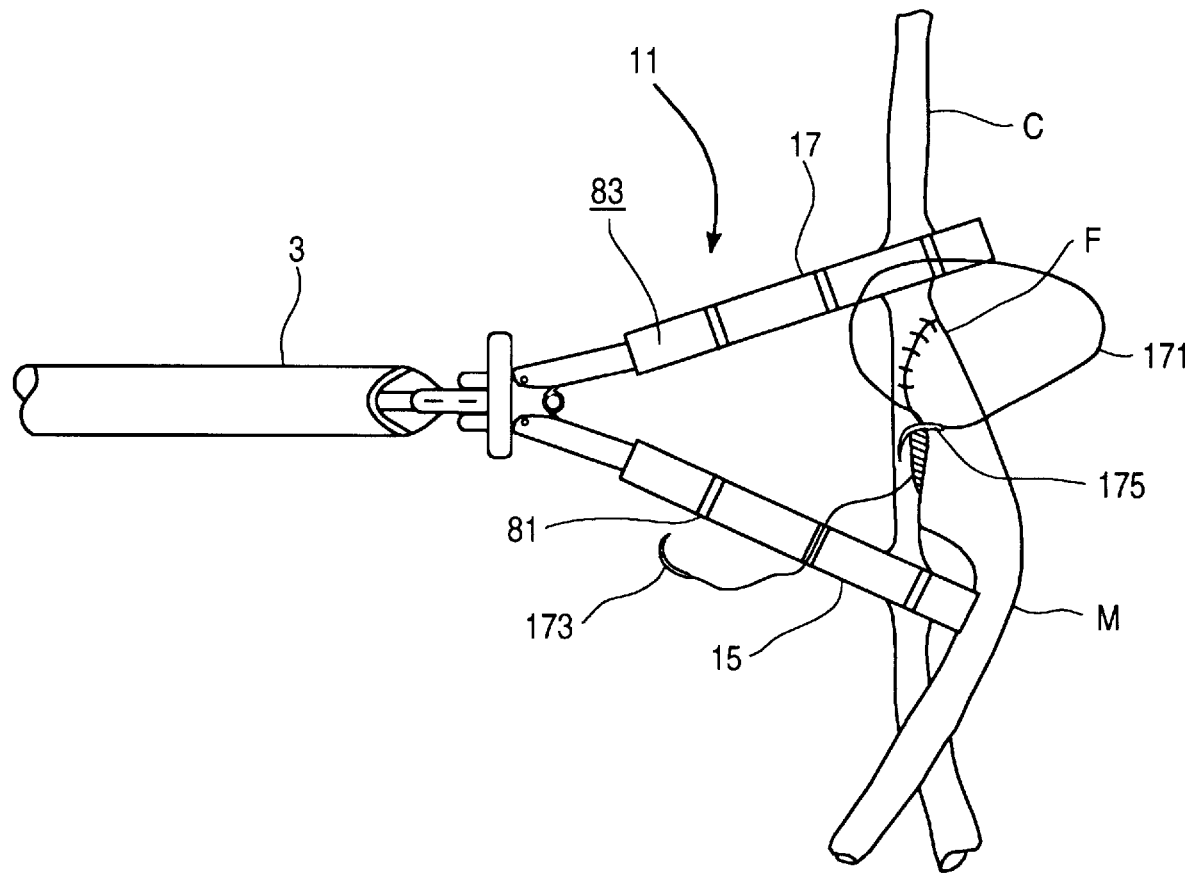
FIG. 6 is a close up view of the surgical site of FIG. 5 illustrating the foot of FIGS. 3A and 3B.

Referring to FIG. 6, arms 15, 17 of foot 11 press against coronary artery C on either side of incision I. If necessary, arms 15, 17 can also be used to stabilize mammary artery M so that free end F is secured with respect to coronary artery C. Preferably, suture holding instrument 169 (not shown in FIG. 6) is used to sew half of free end F around incision I with second needle 175. The surgeon will start sewing at a middle point in suture 171 so that he/she can then sew the other half of free end F around incision I with first needle 173. While the surgeon is utilizing one of the needles, the other one is secured within one of the slots 81 on top surface 83 of arms 15, 17. This allows the surgeon to keep track of suture 171, prevents the two ends of suture 171 from tangling and ensures that the inactive needle does not accidently pierce the surrounding tissue such as the heart. In addition, the surgeon may apply tension to suture 171 by applying tension to the needle 173. This allows the surgeon to reposition or stabilize the surgical site during the operation.

It should be noted that the surgeon could suture the entire free end F to incision I with one needle. In addition, a variety of conventional techniques, other than suturing, can be used to join free end F to incision I such as laser welding, microstapling, and the like.

While the surgeon is forming the anastomosis, blood and other debris may move into the surgical site and obstruct the surgeon's view of the anastomosis. For example, fluids from coronary artery C may exit incision I or fluids and/or tissue structures could migrate into the site from other regions of the thoracic cavity. To clear the surgical site, the surgeon may deliver an irrigation fluid through irrigation lumen 75 and holes 73 into the surgical site.

Figure 7:
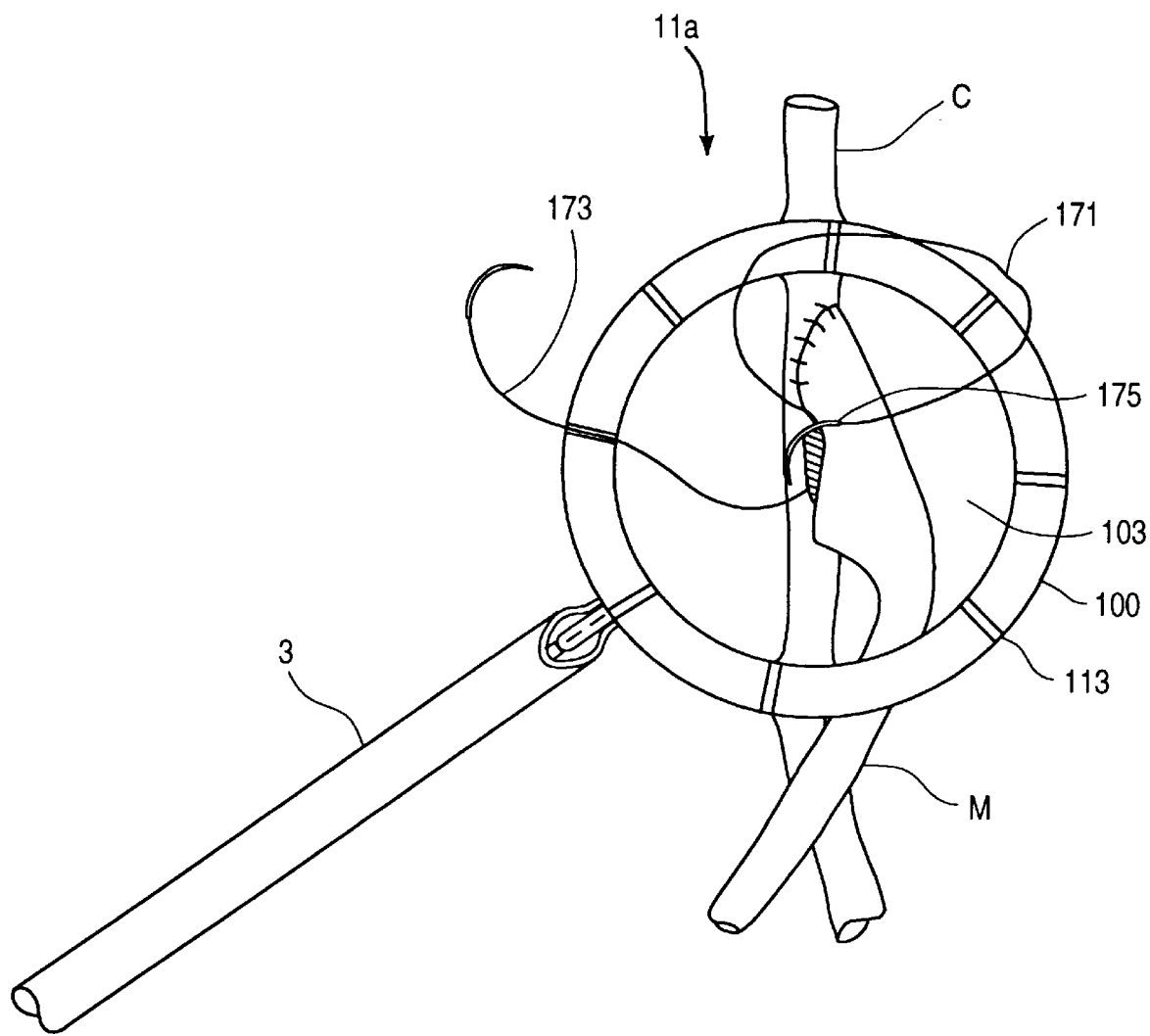
FIG. 7 is a close up view of the surgical site of FIG. 5 illustrating the foot of FIGS. 4A and 4B.

FIG. 7 illustrates ring-shaped foot 11a isolating the surgical site. Annular ring 100 presses against coronary artery C on both sides of incision I without contacting incision I. Mammary artery M is moved into position beneath annular ring 100. Alternatively, annular ring 100 could have a gap or discontinuity (not shown) so that mammary artery M can be moved into position from above annular ring 100 and through hole 103. This allows the surgeon to remove annular ring 100 from the site when the mammary artery M is sutured to coronary artery C. Suture 171 may be held within slots 113 in the same manner described above. Fluid may also delivered through holes 111 to remove debris and/or create a fluid reservoir within hole 103 to submerge the incision I and thereby prevent air from entering coronary artery C.

Referring again to FIG. 5, after the anastomosis has been formed, the surgeon rotates knob 69 to pivot foot 11 so as to align foot 11 with shaft 3. Handle 65 is unclamped and foot 11 is removed from the patient through trocar sleeve 153. The inner walls of trocar sleeve 153 will force arms 15, 17 into the collapsed position so that foot 11 can pass through trocar sleeve 153. The surgeon then removes clamp 161 from mammary artery M and withdraws it from the body cavity. Blood and other fluids are now permitted to flow from mammary artery M into coronary artery C thus bypassing the occluded region in the coronary artery. The downstream free end D of mammary artery M will preferably remain clipped after the operation is complete. The patient's heart may then be restarted by discontinuing infusion of cardioplegic agents, and removing the aortic partitioning device from the ascending aorta. Percutaneous incisions and aortic punctures are closed, cardiopulmonary bypass is discontinued, and the patient is recovered from anesthesia.

It should be understood that the system and method of the present invention could also be used in conjunction with a conventional thoracotomy and open surgical techniques for coronary artery bypass grafting. However, the invention is particularly useful in the minimally-invasive procedures just described.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A method for stabilizing a patient's heart for performing a medical procedure on a coronary artery, the method comprising the steps of:

providing a heat engaging member and a shaft, the shaft having a distal end and a proximal end, the heart engaging member being coupled to the shaft, the heart engaging member including first and second arms each having an atraumatic contact surface adapted for engaging a patient's heart for performing a medical procedure on the patient's heart, the first and second arms each extending from the shaft to a free end, the free ends of the first and second arms being spaced apart for stabilizing a portion of the patient's heart between the first and second arms, the contact surfaces not facing one another and being oriented in generally the same direction;

introducing the heart engaging member into the patient's thoracic cavity;

engaging the patient's heart with the contact surfaces of the first and second arms thereby stabilizing a portion of the patient's heart; and performing a medical procedure on a coronary artery while the portion of the patient's heart is stabilized by the first and second arms.

2. The method of claim 1 wherein:

the providing step is carried out with the first and second arms being movable relative to one another between a collapsed position and an expanded position, the first and second arms being closer to one another when in the collapsed position as compared to the expanded position; and the introducing step being carried out with the first and second arms being in the collapsed position.

3. The method of claim 2, further comprising the step of:

moving the first and second arms from the collapsed position to the expanded position after the introducing step;

the engaging step being carried out with the first and second arms being in the expanded position.

4. The method of claim 1 wherein:

the engaging step is carried out with the contact surfaces being positioned so that an anastomosis site on the coronary artery is positioned between the first and second arms.

5. The method of claim 1 wherein:

the providing step is carried out with the heart engaging member being configured to pivot relative to the shaft.

6. The method of claim 1 wherein:
the providing step is carried out with the shaft including a lumen.

7. The method of claim 6, further comprising the step of:
introducing a fluid into the patient's thoracic cavity through the lumen.

8. The method of claim 6, wherein:
the providing step is carried out with the first and second arms having openings in communication with the lumen.

9. The method of claim 8, further comprising the step of:
coupling the lumen to a vacuum source.

10. The method of claim 1, wherein:
the engaging step is carried out by applying pressure to the patient's heart with the heart engaging member.

11. The method of claim 1, wherein:
the engaging step is carried out so that the heart engaging member engages opposite sides of anastomosis site.

12. The method of claim 1, wherein:
the procedure performing step is a coronary artery bypass.

13. A method for engaging a patient's heart for performing a surgical procedure on a coronary artery, the method comprising the steps of:
providing a heart engaging member and a shaft, the shaft having a distal end and a proximal end, the heart engaging member being movably coupled to the distal end of the shaft, the heart engaging member having an atraumatic contact surface adapted for engaging a patient's heart for performing a surgical procedure on the patient's heart;
introducing the heart engaging member into a patient's thoracic cavity;
engaging the patient's heart with the heart engaging member;
performing a procedure on the patient's heart;
the providing step is carried out with the heart engaging member having first and second engaging portions movably coupled to the shaft, the first and second engaging portions being movable relative to one another between a collapsed position and an expanded position; and
the introducing step being carried out with the fist and second engaging members being in the collapsed position;
the providing step being carried out with the heart engaging member adapted to be positioned on opposite sides of a surgical site on a coronary artery of the patient's heart when in the expanded position;
the moving step being carried out with the first and second members having a gap therebetween when in the expanded position, the gap having a width in a range of 20–40 mm.

14. A method for engaging a patent's heart for performing a surgical procedure on a coronary artery, the method comprising the steps of:
providing a heart engaging member and a shaft, the shaft having a distal end and a proximal end, the heart engaging member being movably coupled to the distal end of the shaft, the heart engaging member having an atraumatic contact surface adapted for engaging a patient's heart for performing a surgical procedure on the patient's heart;
introducing the heart engaging member into a patient's thoracic cavity;
engaging the patient's heart with the heart engaging member; and
performing a procedure on the patient's heart;
the providing step is carried out with the heart engaging member having a suture holder.

15. The method of claim 14, further comprising the step of:
applying a suture to the patient; and
positioning the suture in the suture holder.

16. The method of claim 15 wherein:
the providing step is carried out with the suture holder having at least one slot on an upper surface of the heart engaging member for frictionally engaging the suture, the upper surface being positioned opposite the contact surface.

17. A method for engaging a patient's heart for performing a surgical procedure on a coronary artery, the method comprising the steps of:
providing a heart engaging member and a shaft, the shaft having a distal end and a proximal end, the heart engaging member being movably coupled to the distal end of the shaft, the heart engaging member having an atraumatic contact surface adapted for engaging a patient's heart for performing a surgical procedure on the patient's heart;
introducing the heart engaging member into a patient's thoracic cavity;
engaging the patient's heart with the heart engaging member; and
performing a procedure on the patient's heart;
the providing step is carried out with the heart engaging member being ring-shaped with a central opening;
the engaging step being carried out with the central opening surrounding a surgical site on the patient's coronary artery.

18. The method of claim 17, further comprising the step of:
applying pressure to the heart with the heart engaging member.

19. The method of claim 17, wherein:
the providing step is carried out with the heart engaging member being pivotally coupled to the shaft.

20. The method of claim 17, wherein:
the providing step is carried out with a lumen extending through the shaft, the heart engaging member having outlets coupled to the lumen.

21. The method of claim 20, further comprising the step of:
coupling the lumen to a vacuum source.

22. The method of claim 17 wherein:
the procedure performing step is a coronary artery bypass.

23. A method of stabilizing a surgical site on a patient's heart, comprising the steps of:
introducing a heart engaging member pivotally coupled to a shaft into a patient's thoracic cavity, the heart engaging member having a first engaging portion and a second engaging portion each having a contact surface;
engaging the patient's heart with the contact surfaces such that a surgical site lies between the first and second engaging portions; and
performing a surgical procedure on the surgical site while applying pressure to the patient's heart on opposing sides of the surgical site on the patient's heart with the contact surfaces of the first and second engaging portions thereby stabilizing the surgical site.

24. The method of claim 23 further comprising the step of:

creating an opening in a coronary artery;

the engaging step being carried out so that pressure is applied to the coronary artery to occlude the coronary artery.

25. The method of claim 23 wherein:

the surgical procedure performing step includes connecting a free end of a vessel to the coronary artery at the opening.

26. The method of claim 25 further comprising the step of:

applying pressure to the vessel to stabilize the free end of the vessel with respect to the coronary artery to facilitate connecting the coronary artery and the vessel.

27. The method of claim 23 further comprising the step of:

retaining a first free end of a suture at the heart engaging member while suturing with a second free end of the suture.

28. The method of claim 23 further comprising the step of:

delivering fluid to the surgical site through a lumen in the shaft and an outlet hole in the heart engaging member.

29. The method of claim 23 further including the step of:

creating a fluid reservoir so that the surgical site is immersed in the fluid reservoir.

30. The method of claim 23 wherein:

the introducing step comprises moving the first and second engaging portions into a collapsed configuration and inserting the first and second engaging portions through a percutaneous intercostal penetration.

31. The method of claim 30 further comprising the step of:

moving the first and second engaging portions from the collapsed configuration to an expanded configuration after the introducing step.

32. The method of claim 23 wherein:

the providing step is carried out with the heart engaging member including an annular ring having an opening.

33. The method of claim 23 further including the step of:

viewing an internal portion of the patient's chest through a viewing device extending through an intercostal penetration in the patient.

34. The method of claim 33 further including the step of:

repositioning the patient's heart by applying a force to the heart engaging member so that the coronary artery is visible through the viewing device.

35. The method of claim 23 wherein:

the providing step is carried out so that the contact surface has an arcuate portion that generally conforms to a curvature of the heart.

36. The method of claim 35 wherein the arcuate portion has a radius of curvature between 3 and 5 cm.

37. The method of claim 23, wherein:

the providing step is carried out with the heart engaging member including first and second arms having the first and second engaging portions, respectively.

38. The method of claim 23, wherein:

the providing step is carried out with the heart engaging member having openings coupled to a lumen.

39. The method of claim 38, wherein:

the providing step is carried out with the lumen coupled to a vacuum source.

40. The method of claim 23, wherein:

the procedure performing step is a coronary artery bypass.

\* \* \* \* \*